United States Patent
Wu et al.

(10) Patent No.: US 10,849,632 B2
(45) Date of Patent: Dec. 1, 2020

(54) SURGICAL METHODS OF OSTEOTOMY DEVICE WITH AN IN-VITRO ALIGNMENT COMPONENT

(71) Applicant: A Plus Biotechnology Company Limited, New Taipei (TW)

(72) Inventors: Kai-Hsing Wu, Taipei (TW); Hsiang-Wei Lo, New Taipei (TW); Kun-Jhih Lin, Taichung (TW); Ping-Sheng Yu, Taipei (TW)

(73) Assignee: A Plus Biotechnology Company Limited, New Taipei (TW)

( * ) Notice: Subject to any disclaimer, the term of this patent is extended or adjusted under 35 U.S.C. 154(b) by 125 days.

(21) Appl. No.: 15/927,108

(22) Filed: Mar. 21, 2018

(65) Prior Publication Data
US 2019/0150944 A1    May 23, 2019

(30) Foreign Application Priority Data
Nov. 22, 2017 (TW) .............................. 106140619 A

(51) Int. Cl.
| A61B 17/15 | (2006.01) |
| A61B 17/14 | (2006.01) |
| A61B 17/80 | (2006.01) |
| A61B 17/17 | (2006.01) |
| A61B 17/88 | (2006.01) |
| A61F 2/46  | (2006.01) |

(52) U.S. Cl.
CPC .......... *A61B 17/151* (2013.01); *A61B 17/142* (2016.11); *A61B 17/152* (2013.01); *A61B 17/1764* (2013.01); *A61B 17/8061* (2013.01); *A61B 17/8095* (2013.01); *A61B 17/157* (2013.01); *A61B 17/1767* (2013.01); *A61B 17/809* (2013.01); *A61B 17/8897* (2013.01); *A61F 2/4657* (2013.01)

(58) Field of Classification Search
CPC .... A61B 17/152; A61B 17/151; A61B 17/157
See application file for complete search history.

(56) References Cited

U.S. PATENT DOCUMENTS

| 2002/0165552 | A1* | 11/2002 | Duffner ................ A61B 17/152 606/87 |
| 2008/0262500 | A1* | 10/2008 | Collazo ................ A61B 17/152 606/88 |

* cited by examiner

*Primary Examiner* — Olivia C Chang
(74) *Attorney, Agent, or Firm* — Muncy, Geissler, Olds & Lowe, P.C.

(57) ABSTRACT

The present invention provides a surgical method of osteotomy device with an in-vitro alignment component comprises the steps of: placing a first body component and a second body component on the surface of a bone; engaging an engaging member with a connecting member; inserting at least one aiming bone pin in at least one aiming hole to confirm the cutting direction; inserting at least one fixation bone pins in a plurality of fixation holes to fix the osteotomy device with an in-vitro alignment component; cutting along a guide slot to produce an osteotomy; spreading the osteotomy; placing a bone plate to maintain the osteotomy.

15 Claims, 14 Drawing Sheets

SURGICAL METHODS OF OSTEOTOMY DEVICE WITH AN IN-VITRO ALIGNMENT COMPONENT

BACKGROUND OF THE INVENTION

Technical Field

The present invention generally relates to a surgical method, and more particularly, to a surgical method of osteotomy device with an extracorporeal alignment component.

Description of Related Art

The human knee is a relatively complex mechanical joint. It is the largest joint in the human body, comprised of the two longest bones in the body, the femur and the tibia. The ends of the bones are covered with articular cartilage. The role of articular cartilage minimizes stress on subchondral bone, and reduces the friction on the joint surface.

However, under the continuous development of science and technology, human average life-span continues to be extended. But the articular cartilage is gradually worn with the aging of body. It causes the occurrence of degenerative joint disease called osteoarthritis. For patients with knee osteoarthritis in the observation of the X-ray, surgeons can find the uneven of joint surface, narrowed joint space and bone spurs. These pathological phenomena will cause the patients to produce pain, swelling, joint deformation, stiffness and other symptoms. This is the inevitable trend of physiological aging, it seems that the older the more likely to encounter the disease.

Taking knee for example, most common treatment of knee osteoarthritis is to implant the artificial joint to replace the knee joint surface, but large amount of soft tissue and hard tissue should be removed from the femur, the tibia and the patella to provide the fixation of metal and polyethylene implants. Due to the wear of the polyethylene component, the longevity of the artificial joint replacement is often complicated by postoperative infection, osteolysis and bone resorption, which results in the possibility of a revision surgery. Furthermore, in early-stage knee osteoarthritis, only the medial articular surface is affected. It is not necessary to replace all articular surface by artificial knee components. High tibial osteotomy is an alternative option for patients with medial knee osteoarthritis.

High tibial osteotomy is performed by a bony cutting plane in the proximal tibia of the knee on the medial side and making an opening wedge by spreading the bony cutting site. Finally, the construct is supported by bone plate fixation. Thus the mechanical axis of the low limb can be corrected. In this procedure, the cartilage and bone stock around the knee joint are preserved. For the patients with medial knee osteoarthritis, it is a good option for surgical treatment.

The success for high tibial osteotomy relies on an appropriate bone cut including the cutting position, direction, depth, and the spreading height which are related to the correction angle. This surgery is highly technical demanded. At present, the surgeons perform the procedure based upon preoperative roentgenology images and their experience without any reference or guiding device. Moreover, the condition of genu varum or deformity is different for each patient. The above-mentioned parameters are also different for each patient. A personalized surgical instrument is needed for a better control of the deformity correction.

The prior art of the present invention is TWM536526U. But, there is still room for improvement. For examples, it cannot take a non-invasive assessment of the correction angle when the surgery is performed, it cannot predict whether the placement (orientation/position) of the osteotomy device is correct, it cannot directly fix the placement of the osteotomy device, it may result in over-cutting when starting to cut. The inventor of the present invention has further expanded its function and improved many of the techniques present in the prior art. Therefore, the inventor developed the surgical method of osteotomy device with an extracorporeal alignment component, the expansion of the function and improvement of the technology will be described in detail in the specification.

SUMMARY OF THE INVENTION

In view of the foregoing problems, the present invention provides a surgical method of osteotomy device with an extracorporeal alignment component. It is used to guide a saw blade to perform high tibial osteotomy, but not limited to, the surgical method of osteotomy device with an extracorporeal alignment component can be used for other bones, such as: femur, fibula, humerus, ulna, radius, clavicle, scapula and so on. The tibia is described in the preferred embodiment of the present invention. The device design features to assist the surgeon to determine the cutting position, direction, depth, and the spreading height precisely. Moreover, it can take a non-invasive assessment of the angle during surgery, it can predict whether the placement (orientation/position) of the osteotomy device is correct, it can directly maintain the orientation/position of the osteotomy device and it can avoid over-cutting. The accuracy of the tibial osteotomy after the operation of the present invention will be improved. Each device is tailored to the patient.

The present invention provides a surgical method of osteotomy device with an extracorporeal alignment component. The surgical method of osteotomy device with an extracorporeal alignment component is used to guide a saw blade to perform high tibial osteotomy, but not limited to, it can also be applied to other bones. According to the embodiment of the present invention, the surgical method of osteotomy device with an extracorporeal alignment component comprises the steps of: placing a first body component and a second body component on the surface of a bone; engaging an engaging member with a connecting member; inserting at least one aiming bone pin in at least one aiming hole to confirm the cutting direction; inserting at least one bone pins in a plurality of fixation holes to fix the osteotomy device with an extracorporeal alignment component; cutting along a guide slot to produce an osteotomy; spreading the osteotomy; placing a bone plate to maintain the opening. Wherein the osteotomy device with an extracorporeal alignment component comprises: a first body component, a second body component and an extracorporeal alignment component. The first body component has an upper guide fin for forming a cutting track; the second body component has a lower guide fin below the upper guide fin, a guide slot is formed between the upper guide fin and the lower guide fin for guiding a saw blade to perform a bone cutting. The guide slot has a connecting member for connecting the upper guide fin and the lower guide fin. The extracorporeal alignment component has an engaging member and at least one aiming hole. The engaging member is engaged with the connecting member. The aiming hole is used to confirm the direction of cutting.

According to the embodiment of the present invention, wherein the step of inserting the aiming bone pin in the aiming hole comprises: inserting a bone pin in an angle fixation hole to fix the orientation of the osteotomy device with an extracorporeal alignment component. Wherein the extracorporeal alignment component has an engaging member, at least one aiming hole and an angle fixation hole. The engaging member is engaged with the connecting member. The aiming hole is used to confirm the direction of cutting. The angle fixation hole is disposed in the engaging member, the orientation/position of the osteotomy device with an extracorporeal alignment component is fixed to the bone by using a bone pin.

According to the embodiment of the present invention, wherein the step of cutting along the guide slot comprises: cutting along a lateral guide fin. Then, the step of cutting along a lateral guide fin comprises: inserting into at least one osteotome. Wherein the first body component has an upper guide fin, a lateral guide fin and a first correcting through-hole. The lateral guide fin is disposed at the end of the upper guide fin for forming a cutting track. The first correcting through-hole is connected to the first body component by a first bar. The second body component has a lower guide fin, an extended barrier plate and a second correcting through-hole. The lower guide fin disposed below the upper guide fin. The extended barrier plate is disposed at the end of the lower guide fin to prevent over-cutting by the saw blade. The second correcting through-hole is connected to the second body component by a second bar. A guide slot is formed between the upper guide fin and the lower guide fin for guiding a saw blade to perform a bone cutting. The guide slot has a connecting member for connecting the upper guide fin and the lower guide fin.

According to the embodiment of the present invention, wherein the step of opening the osteotomy comprises: inserting an alignment bar in the longitudinal axis of the first correcting through-hole and the longitudinal axis of the second correcting through-hole. Then, the step of inserting the alignment bar comprises: fixing the height of the osteotomy by a spreader. Wherein the osteotomy device with an extracorporeal alignment component has a correction angle between the longitudinal axes of the first correcting through-hole and the second correcting through-hole. When the correction angle of osteotomy is the same as that of the preoperative planning, the longitudinal axes of the first correcting through-hole and the second correcting through-hole will coincide and an alignment bar can pass through both through-holes. The aiming hole confirms the direction of cutting by passing through at least one aiming bone pin. The surfaces of the first body component and the second body component have a plurality of fixation holes, the osteotomy device with an extracorporeal alignment component is fixed on the surface of the bone by inserting at least one bone pin in the plurality of fixation holes.

Compared with the conventional technique, the osteotomy device with an extracorporeal alignment component is manufactured by three-dimensional printing (3D printing) according to the patient's bony CT data and the evaluation of the ideal cutting position and angle. The outer surface of the device can fit to the patient's bony anatomy, such as: femur, fibula, humerus, ulna, radius, clavicle, scapula and so on. The surgeon can perform the first bone cutting via the guide slot. The guide slot helps the surgeon perform the operation accurately. It is also a reference for evaluating the direction and depth of bone cutting. The lateral guide fin provides the other reference of the second bone cutting. The extracorporeal alignment component works for non-invasive assessment of the cutting direction during surgery, it can predict whether the placement (orientation/position) of the osteotomy device is correct and fix it in position. The extended barrier plate can avoid over-cutting. The present invention further improves the previous osteotomy device.

BRIEF DESCRIPTION OF THE DRAWINGS

The components, characteristics and advantages of the present invention may be understood by the detailed description of the preferred embodiments outlined in the specification and the drawings attached.

DETAILED DESCRIPTION

Some preferred embodiments of the present invention will now be described in greater detail. However, it should be recognized that the preferred embodiments of the present invention are provided for illustration rather than limiting the present invention. In addition, the present invention can be practiced in a wide range of other embodiments besides those explicitly described, and the scope of the present invention is not expressly limited except as specified in the accompanying claims. The layout of components may be more complicated in practice.

The present invention provides a surgical method of osteotomy device with an extracorporeal alignment component which can be used in various osteotomy, correction operation or reduction surgery. The surgical method of osteotomy device with an extracorporeal alignment component can be used for other bones 760, such as: femur, fibula, humerus, ulna, radius, clavicle, scapula and so on. In the present embodiment, the surgical method of osteotomy device with an extracorporeal alignment component is used to guide a saw blade 820 to perform high tibial osteotomy of tibia.

Figure 1:
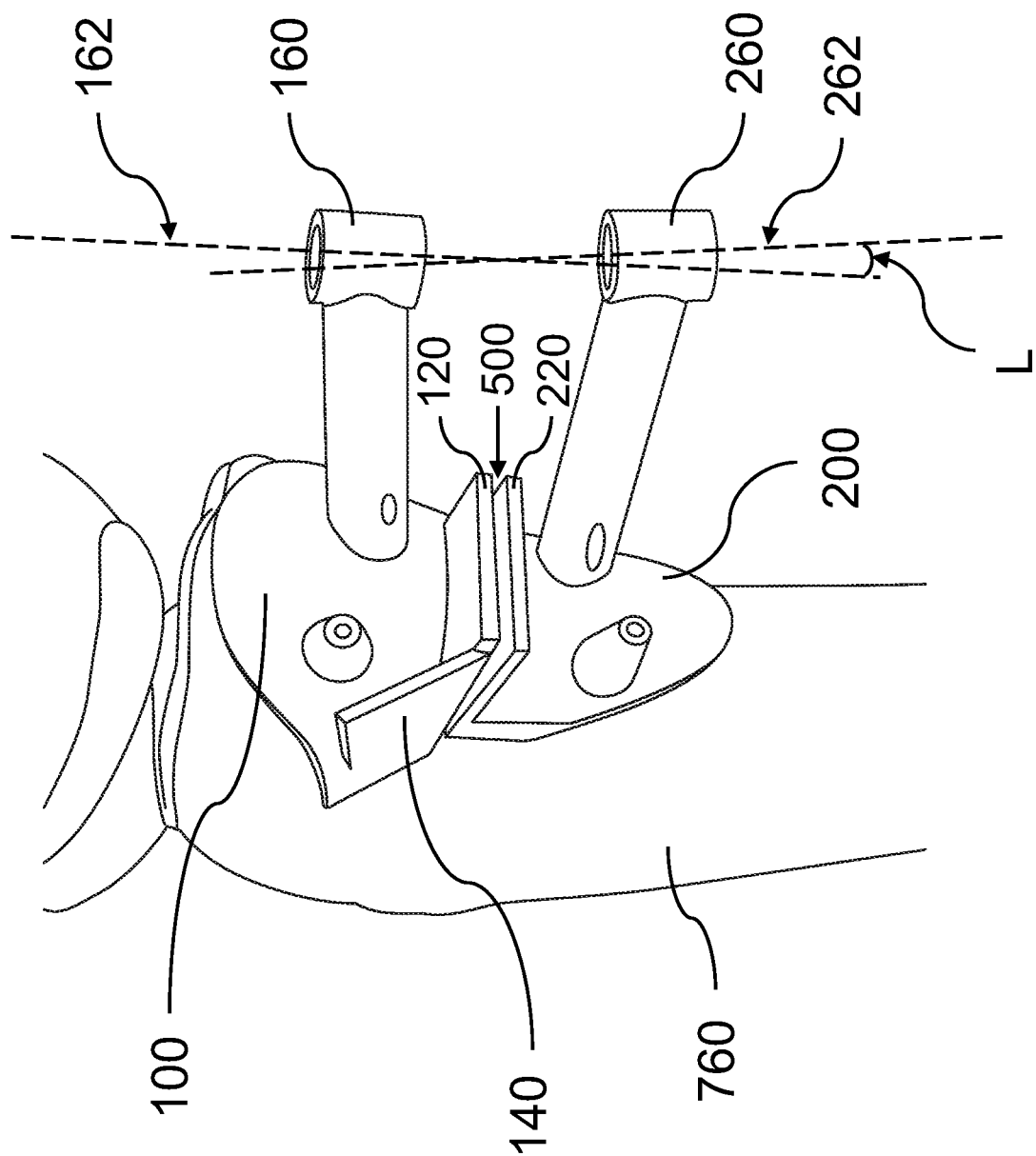
FIG. 1 illustrates the step of placing a first body component and a second body component on the surface of the bone.
Figure 2:
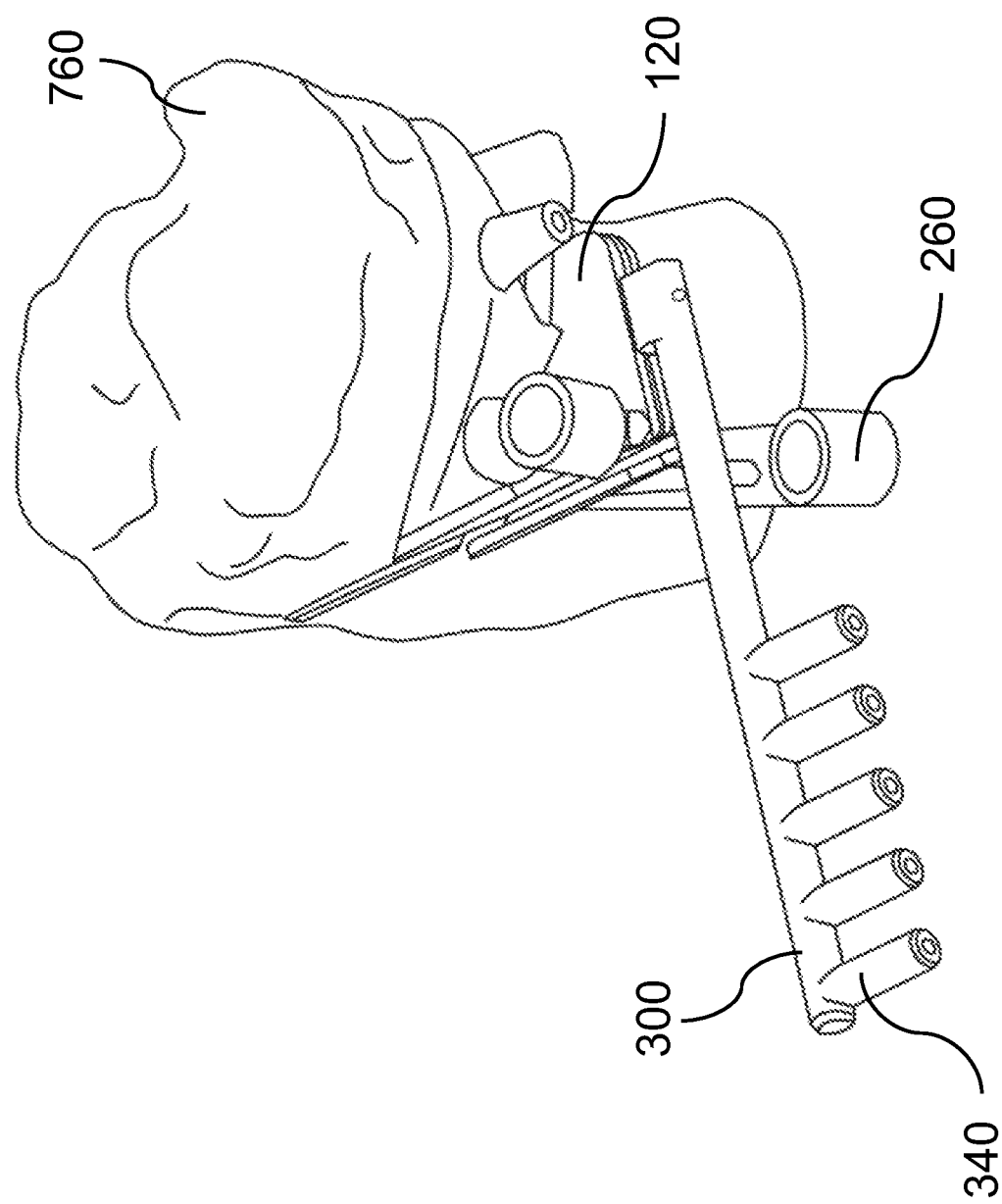
FIG. 2 illustrates the step of engaging an engaging member with a connecting member.
Figure 3:
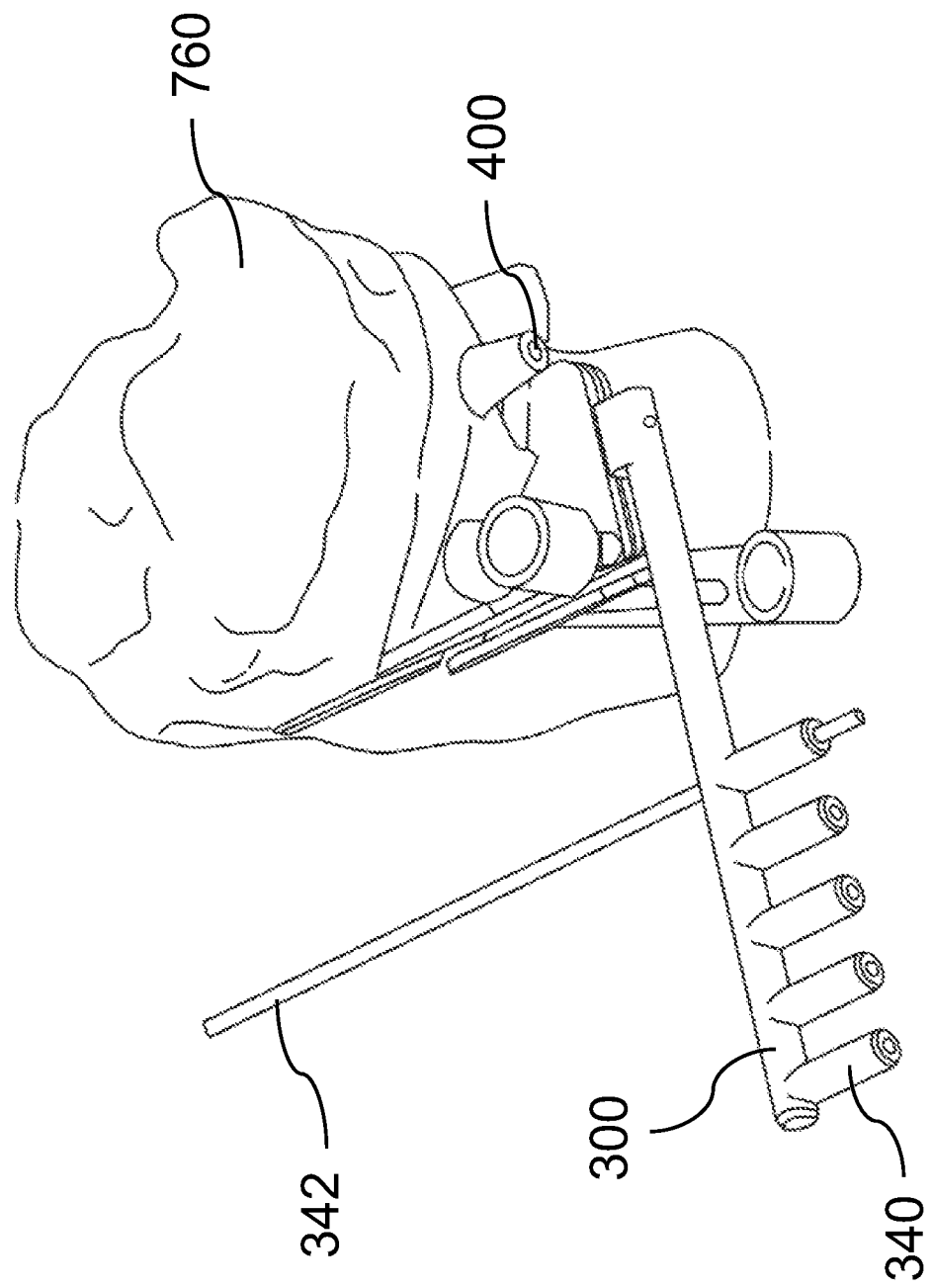
FIG. 3 illustrates the step of inserting at least one aiming bone pin in at least one aiming hole to confirm the cutting direction.
Figure 5:
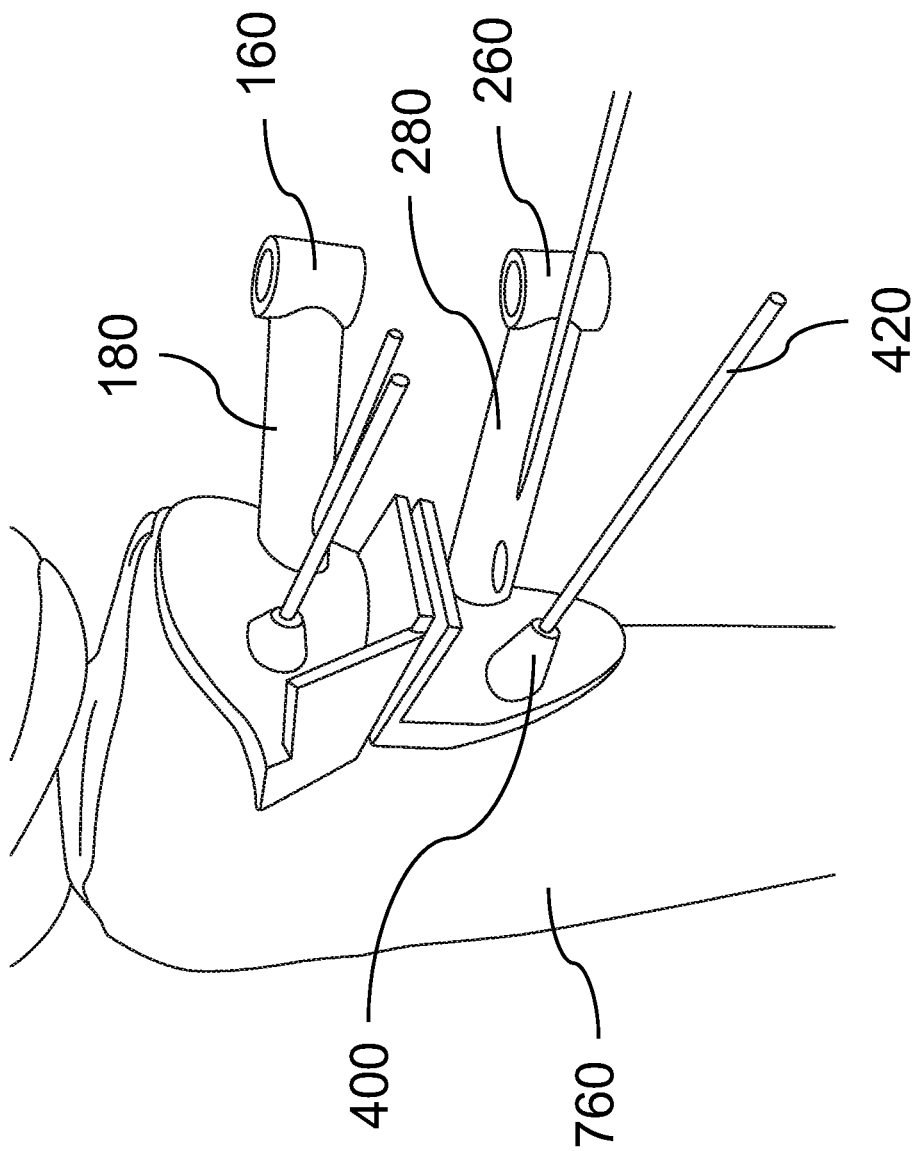
FIG. 5 illustrates the step of inserting at least one bone pin in a plurality of fixation holes to fix the osteotomy device with an extracorporeal alignment component.
Figure 6:
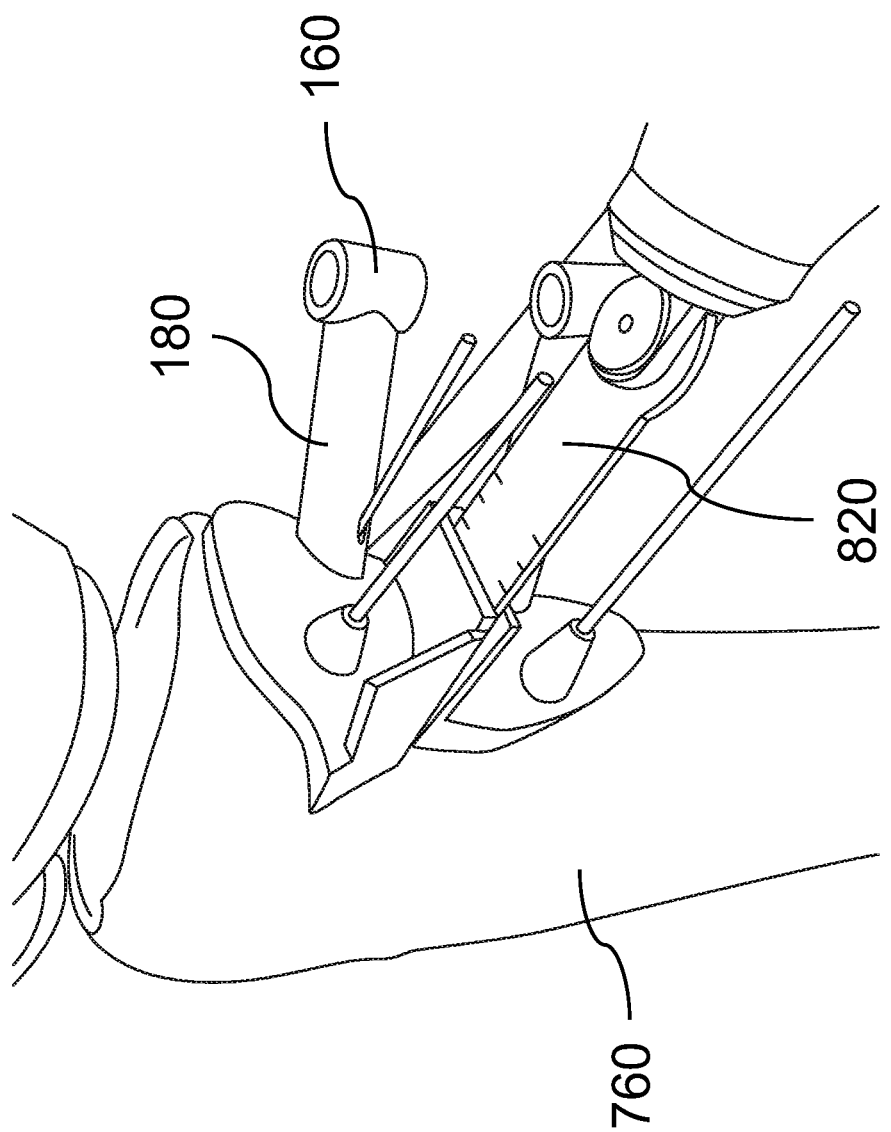
FIG. 6 illustrates the step of cutting along a guide slot to produce an osteotomy.
Figure 9:
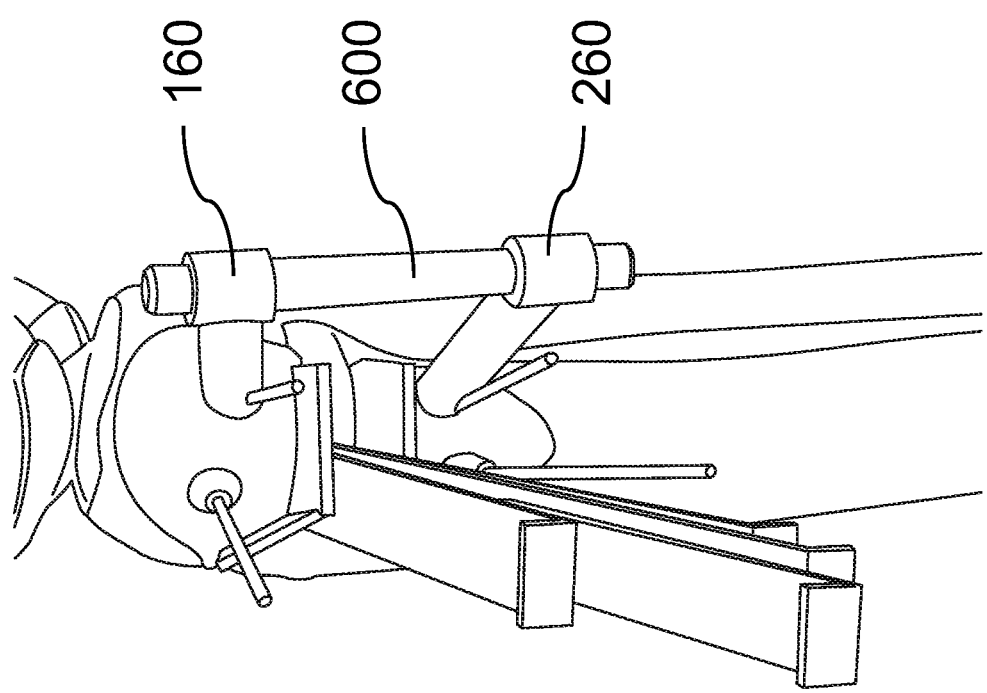
FIG. 9 illustrates the step of opening the osteotomy and inserting an alignment bar through the first through-hole and the second through-hole.
Figure 11:
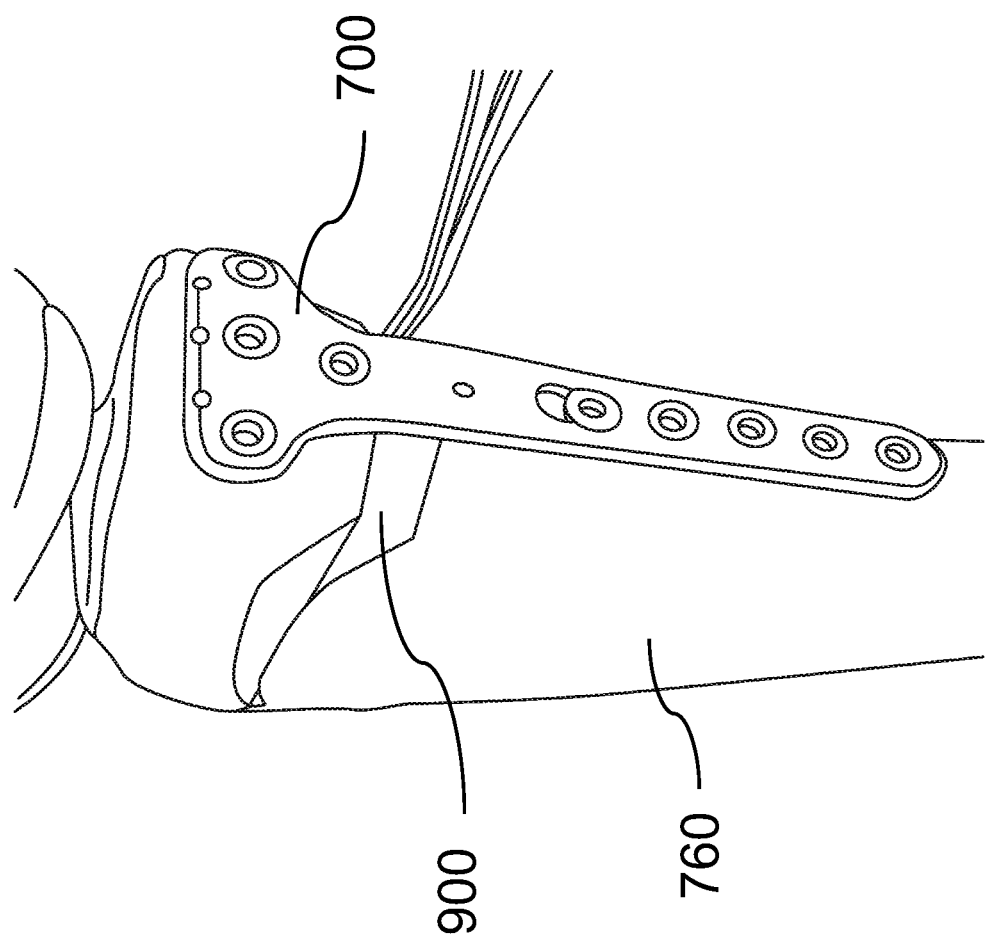
FIG. 11 illustrates the step of placing a bone plate for fixation of bone osteotomy.
Figure 12:
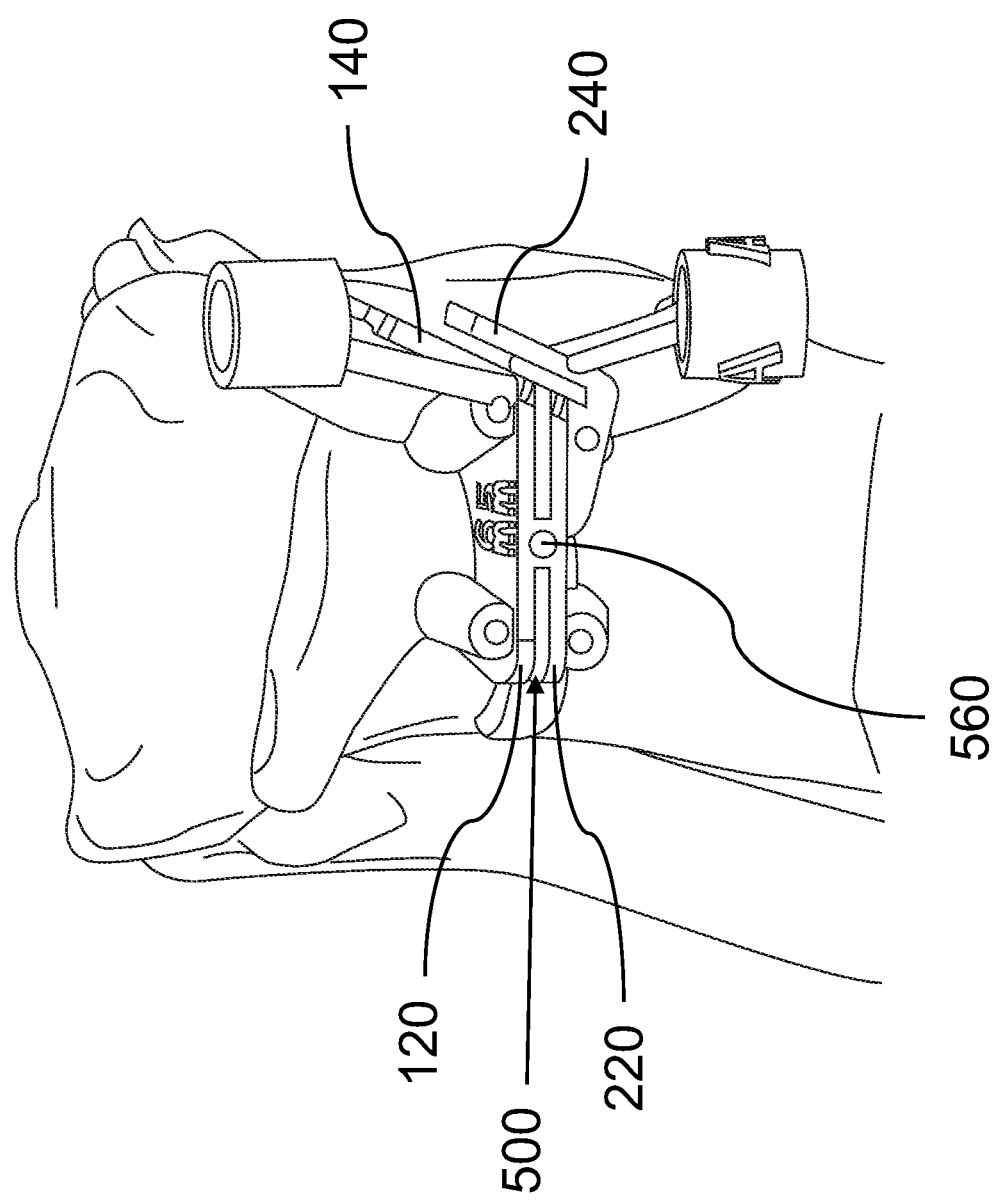
FIG. 12 illustrates a lateral view of osteotomy device without an extracorporeal alignment component.
Figure 13:
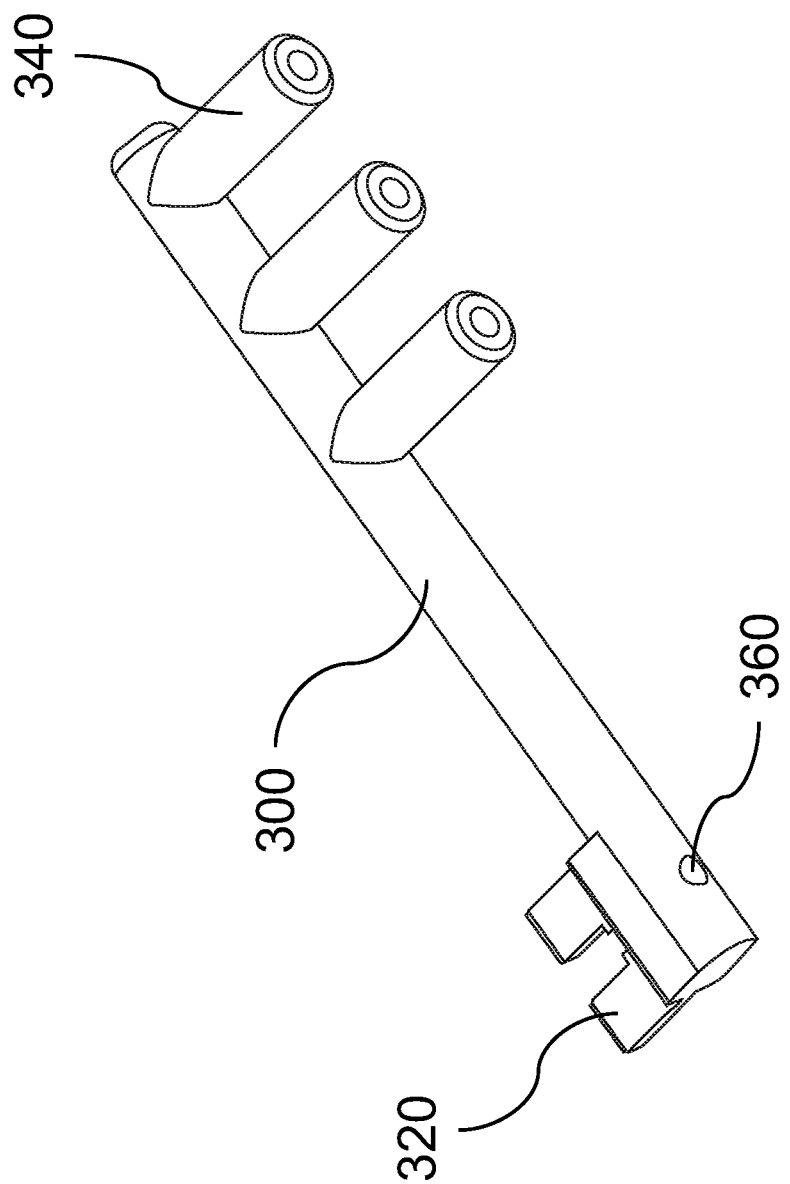
FIG. 13 illustrates an extracorporeal alignment component.

Please refer to FIG. 1, FIG. 2, FIG. 3, FIG. 5, FIG. 6, FIG. 9, FIG. 11, FIG. 12 and FIG. 13. FIG. 1 illustrates the step of placing a first body component 100 and a second body component 200 on the surface of a bone 760. FIG. 2 illustrates the step of engaging an engaging member 320 with a connecting member 560. FIG. 3 illustrates the step of inserting at least one aiming bone pin 342 in at least one aiming hole 340 to confirm the cutting direction. FIG. 5 illustrates the step of inserting at least one bone pin 420 in a plurality of fixation holes 400 to fix the osteotomy device with an extracorporeal alignment component. FIG. 6 illustrates the step of cutting along a guide slot 500 to produce an osteotomy 900. FIG. 9 illustrates the step of opening the osteotomy 900 and inserting an alignment bar 600 in the first longitudinal axis 162 of the first through-hole 160 and the second longitudinal axis 262 of the second through-hole 260. FIG. 11 illustrates the step of placing a bone plate 700 to fix the osteotomy 900. FIG. 12 illustrates a lateral view of osteotomy device without an extracorporeal alignment component 300. FIG. 13 illustrates an extracorporeal alignment component 300.

In one embodiment of the present invention, the surgical method of osteotomy device with an extracorporeal alignment component comprises the steps of: placing a first body component 100 and a second body component 200 on the surface of a bone 760; engaging an engaging member 320 with a connecting member 560; inserting at least one aiming bone pin 342 in at least one aiming hole 340 to confirm the cutting direction; inserting at least one bone pin 420 in a plurality of fixation holes 400 to fix the osteotomy device with an extracorporeal alignment component; cutting along a guide slot 500 to produce an osteotomy 900; opening the osteotomy 900; placing a bone plate 700 to fix the osteotomy 900. When the osteotomy device with an extracorporeal alignment component is arranged on the surface of the tibia, the extracorporeal alignment component 300 is mounted on the connecting member 560 of the osteotomy device through the engaging member 320. The engaging member 320 and the aiming hole 340 are respectively located at both ends of the extracorporeal alignment component 300. When the osteotomy device with an extracorporeal alignment component is placed on the bone 760 surface, the extracorporeal alignment component 300 has a rectangular appearance and the extracorporeal alignment component 300 is placed laterally on the osteotomy device with an extracorporeal alignment component so that the aiming hole 340 can be located on the outside of human body. The orientation and the position of the osteotomy device with an extracorporeal alignment component can be evaluated in a noninvasive manner by the aiming hole 340. Therefore, it is possible to predict whether the orientation/position of the osteotomy device with an extracorporeal alignment component is correct. Then, the surgeon inserts the saw blade 820 and starts cutting according to the cutting position guided by the upper guide fin 120 and the lower guide fin 220 of the osteotomy device. The surgeon can use the upper guide fin 120 and the lower guide fin 220 as a reference for the calculation of the depth of cut. In another way, make a mark on the saw blade 820, the surgeon can check the cutting depth by eyes.

Wherein the osteotomy device with an extracorporeal alignment component comprises: a first body component 100, a second body component 200 and an extracorporeal alignment component 300. The first body component 100 has an upper guide fin 120 for forming a cutting track; the second body component 200 has a lower guide fin 220 disposed below the upper guide fin 120, a guide slot 500 is formed between the upper guide fin 120 and the lower guide fin 220 for guiding a saw blade 820 to perform a bone cutting. The guide slot 500 has a connecting member 560 for connecting the upper guide fin 120 and the lower guide fin 220. The extracorporeal alignment component 300 has an engaging member 320 and at least one aiming hole 340. The engaging member 320 is engaged with the connecting member 560. The aiming hole 340 confirms the direction of cutting by passing through at least one aiming bone pin 342. When the operation is performed, the surgeon can directly cut the connecting member 560 with the bone saw. In addition, the surfaces of the first body component 100 and the second body component 200 have a plurality of fixation holes 400, the osteotomy device with an extracorporeal alignment component is fixed on the surface of the bone 760 by inserting at least one fixation bone pins 420 in the plurality of fixation holes 400. Whereby the osteotomy device with an extracorporeal alignment component is fixed more firmly to the surface of the bone 760. It can avoid the saw blade 820 causing the osteotomy device with an extracorporeal alignment component to move during bone cutting. It makes the cutting position more accurate. Furthermore, the aiming hole 340 is cylindrical in the present embodiment, but not limited to, it may be changed to other shapes as necessary. The aiming hole 340 is sequentially attached to the extracorporeal alignment component 300 by an end of the extracorporeal alignment component 300. Its cylindrical design allows the aiming bone pin 342 to pass through. It is possible to determine whether the osteotomy device with an extracorporeal alignment component of the present invention is set at the correct orientation/position by the guidance of the aiming bone pin 342. The aiming bone pin 342 is the extracorporeal guideline of the orientation/position of the device. It is a non-invasive assessment.

Figure 4:
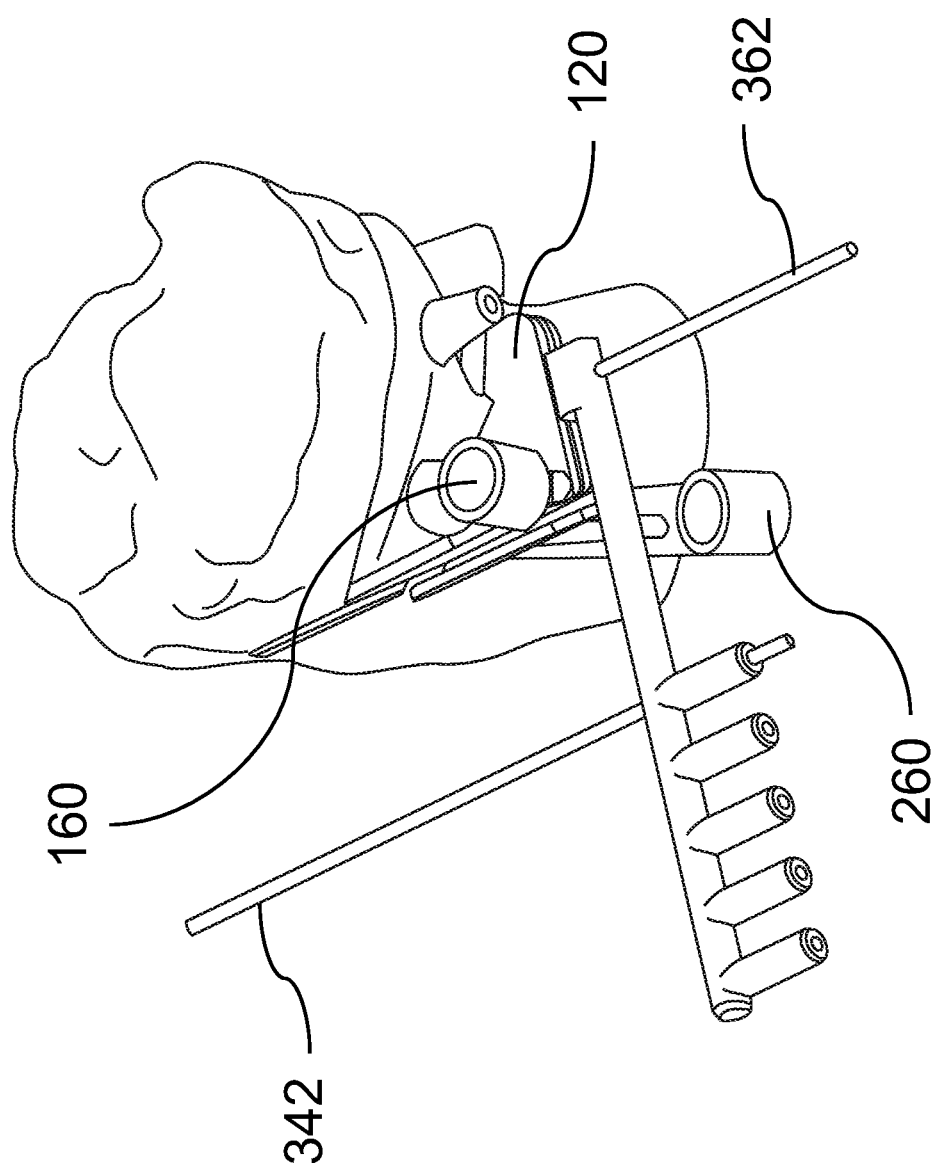
FIG. 4 illustrates the step of inserting a bone pin in an angle fixation hole to fix the orientation of the osteotomy device with an extracorporeal alignment component.

Please refer to FIG. 4. FIG. 4 illustrates the step of inserting an angle fixation bone pin 362 in an angle fixation hole 360 to fix the orientation of the osteotomy device with an extracorporeal alignment component.

In another embodiment of the present invention, wherein the step of inserting the aiming bone pin 342 in the aiming hole 340 comprises: inserting an angle fixation bone pin 362 in an angle fixation hole 360 to fix the orientation/position of the osteotomy device with an extracorporeal alignment component. When the aiming hole 340 confirms that the orientation/position of the osteotomy device with an extracorporeal alignment component is correct, the osteotomy device can be fixed the orientation/position on the bone 760 directly by inserting the angle fixation bone pin 362 from the angle fixation hole 360 of the extracorporeal alignment component 300. Compared with the osteotomy device in the prior art, the present invention will have a more precise cutting orientation and position. The precise cutting is a very important point in osteotomy. Because the correction angle of the bone 760 is based on it. Therefore, it affects the correction of the biomechanical axis of the low limb.

Wherein the extracorporeal alignment component 300 has an engaging member 320, at least one aiming hole 340 and an angle fixation hole 360. The engaging member 320 is engaged with the connecting member 560. The aiming hole 340 is used to confirm the direction of cutting. The angle fixation hole 360 is disposed in the engaging member 320, the orientation/position of the osteotomy device with an extracorporeal alignment component is fixed to the bone 760 by using an angle fixation bone pin 362. In order to reinforce the fixation strength of the osteotomy device with an extracorporeal alignment component on the bone 760 surface, at least one fixation bone pins 420 can be inserted in the fixation holes 400 after the osteotomy device with an extracorporeal alignment component is fixed the orientation/position on the bone 760 directly by inserting the angle fixation bone pin 362 from the angle fixation hole 360 of the extracorporeal alignment component 300.

Figure 7:
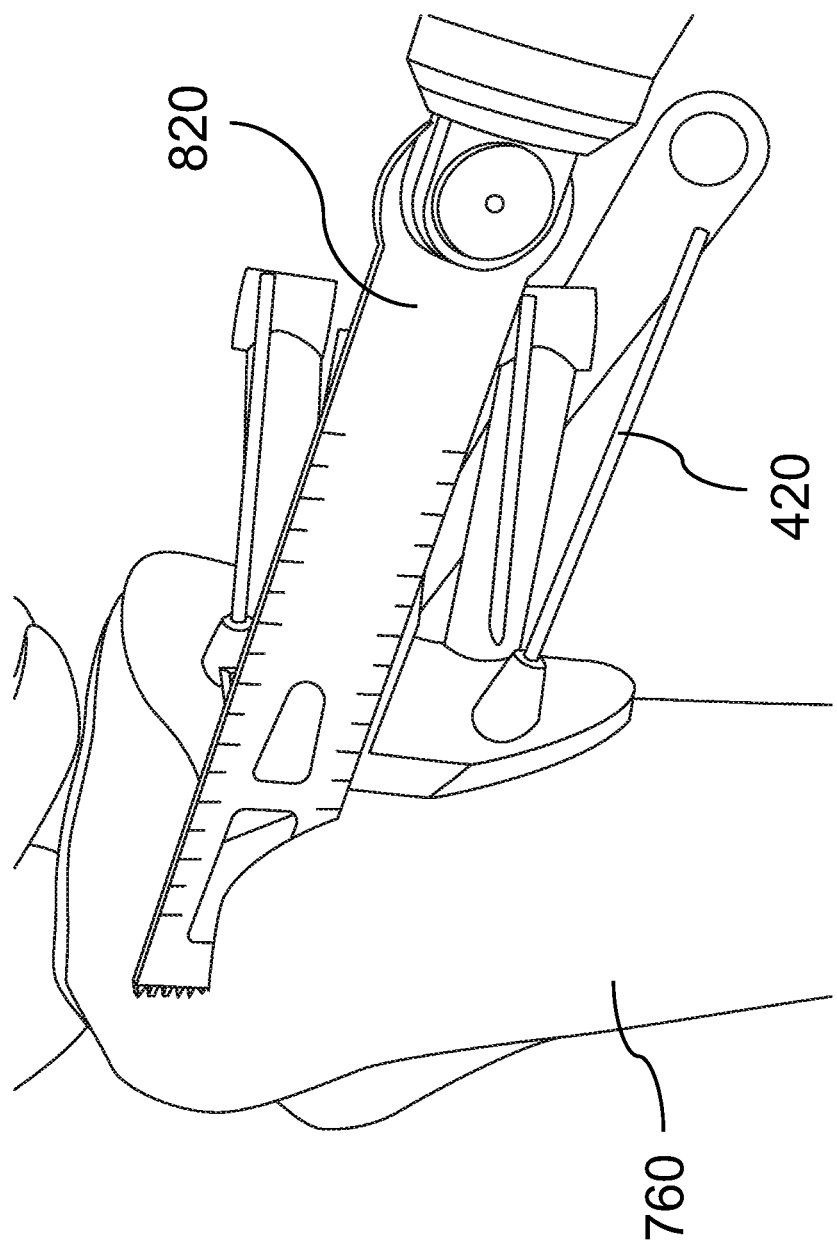
FIG. 7 illustrates the step of cutting along a lateral guide fin.
Figure 8:
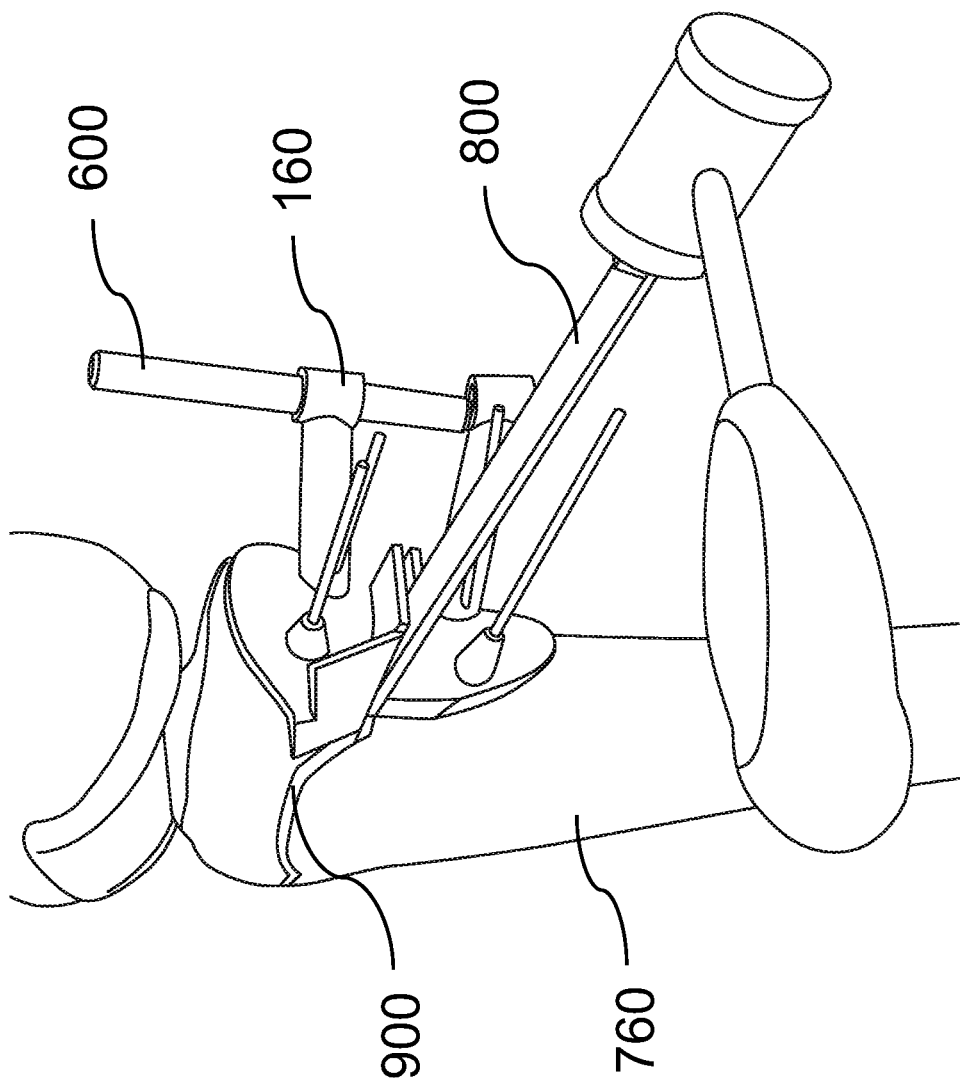
FIG. 8 illustrates the step of inserting into at least one osteotome.

Please refer to FIG. 7 and FIG. 8. FIG. 7 illustrates the step of cutting along a lateral guide fin 140. FIG. 8 illustrates the step of inserting at least one osteotome 800.

In one embodiment of the present invention, wherein the step of cutting along the guide slot 500 comprises: cutting along a lateral guide fin 140. Then, the step of cutting along a lateral guide fin 140 comprises: inserting at least one osteotome 800. The surgeon can use the upper guide fin 120 and the lower guide fin 220 as a reference for the calculation of the depth of cut. The saw blade 820 cuts to a predetermined depth and cuts along the upper guide fin 120 and the lower guide fin 220 to the inside of the human body. Then, it cuts along the second cutting position guided by the lateral guide fin 140 to produce an oblique osteotomy 900. Moreover, the surgeon inserts the osteotome 800 to spread the osteotomy 900.

Wherein the first body component 100 has an upper guide fin 120 and a lateral guide fin 140. The lateral guide fin 140 is disposed at the end of the upper guide fin 120 for forming a cutting track. The lateral guide fin 140 is used to guide the saw blade 820 to perform a cutting procedure of the second cutting position. The second body component 200 has a lower guide fin 220 and an extended barrier plate 240. The lower guide fin 220 is disposed below the upper guide fin 120. The extended barrier plate 240 is disposed at the end of the lower guide fin 220 to prevent over-cutting by the saw blade 820 on the lateral guide fin 140. The upper guide fin 120 and the lower guide fin 220 extend outwardly from the first body component 100 and the second body component 200, respectively. A guide slot 500 is formed between the upper guide fin 120 and the lower guide fin 220 for guiding the saw blade 820 to perform a cutting procedure of the first cutting position. The guide slot 500 has a connecting member 560 for connecting the upper guide fin 120 and the lower guide fin 220. The upper guide fin 120, the lower guide fin 220 and the lateral guide fin 140 are used to form the cutting track for operating high tibial osteotomy. In the previous technology of osteotomy device, it is found that the position of the lateral guide fin 140 often occurs over-cutting in the surgical operation. If the surgeon cuts more than a lot, the extra osteotomy 900 will make the bones 760 become more fragile. It may cause bones 760 to break when fixing the bone plate 700. So that the patient's recovery period is prolonged. In order to avoid over-cutting, the present invention further improves the design. An extended barrier plate 240 is added to the second body component 200 relative to the lateral guide fin 140. When the saw blade 820 cuts to a predetermined position, it can be blocked by the extended barrier plate 240 to avoid over-cutting. The entire cutting track becomes complete. In the practice of osteotomy, the present invention is carried out more precisely in accordance with the originally intended plan. It can prevent the occurrence of defects and shorten the recovery period of patients.

Figure 10:
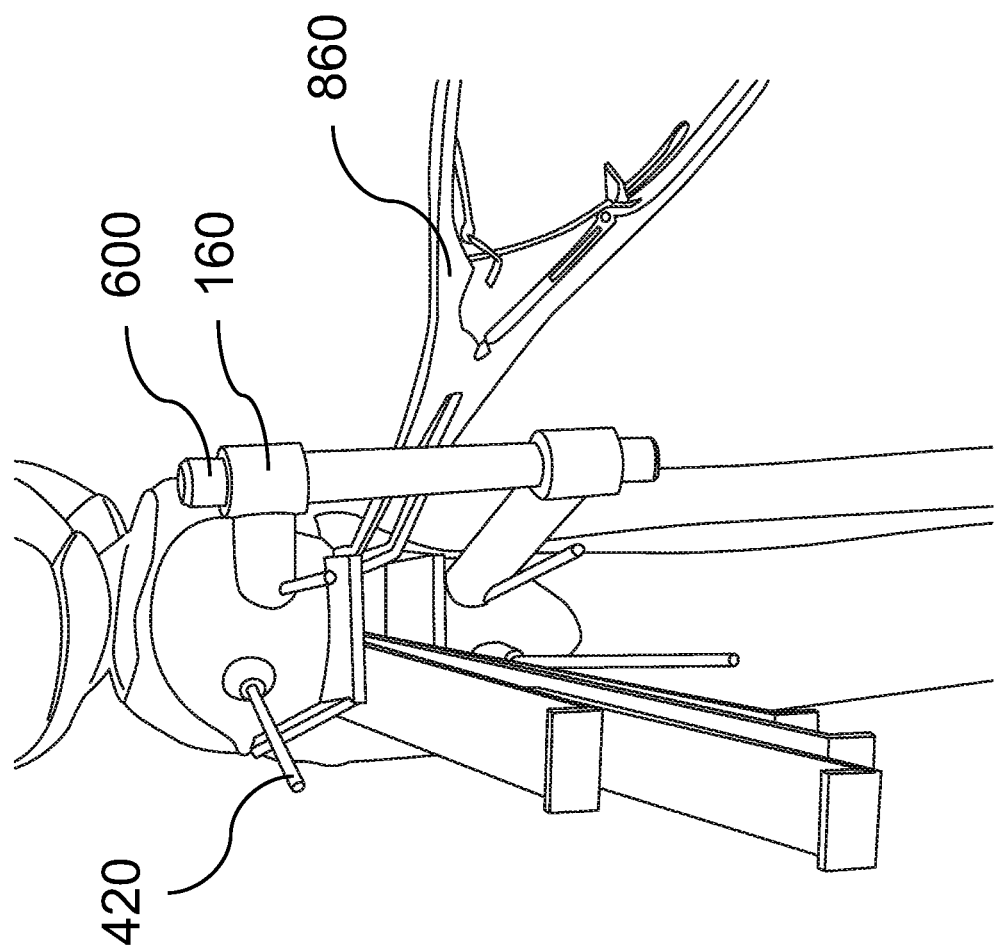
FIG. 10 illustrates the step of maintaining the opening height of the osteotomy by a spreader.
Figure 14:
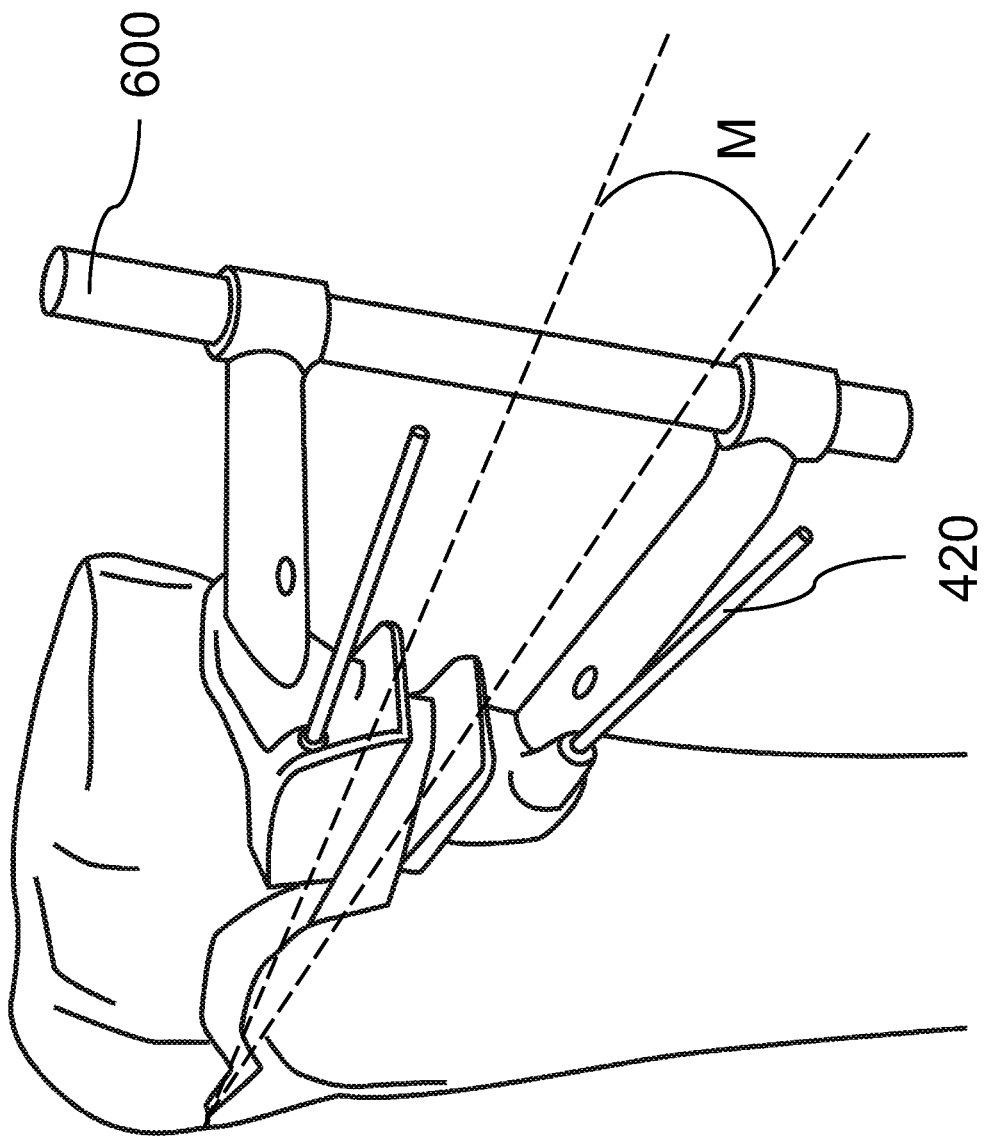
FIG. 14 illustrates that the bone is opened to the correction angle by the first body component and the second body component

Please refer to FIG. 9, FIG. 10 and FIG. 14. FIG. 9 illustrates the step of spreading the osteotomy 900 and inserting an alignment bar 600 in the longitudinal axis 162 of the first correcting through-hole 160 and the longitudinal axis 262 of the second correcting through-hole 260. FIG. 10 illustrates the step of fixing the height of the osteotomy 900 by a spreader 860. FIG. 14 illustrates that the bone 760 is opened to the correction angle M by the first body component 100 and the second body component 200.

In another embodiment of the present invention, wherein the step of spreading the osteotomy 900 comprises: inserting an alignment bar 600 in the longitudinal axis 162 of the first correcting through-hole 160 and the longitudinal axis 262 of the second correcting through-hole 260. Then, the step of inserting the alignment bar 600 comprises: fixing the height of the osteotomy 900 by a spreader 860. The saw blade 820 cuts to a predetermined depth and cuts along the upper guide fin 120 and the lower guide fin 220 to the inside of the human body. Then, it cuts along the second cutting position guided by the lateral guide fin 140 to produce an oblique osteotomy 900. After the osteotomy 900 is cut, the first cutting position of the tibia is opened to the correction angle of preoperative planning where the osteotomy device with an extracorporeal alignment component is fixed to the tibia. The alignment bar 600 is then inserted through the first correcting through-hole 160 and the second correcting through-hole 260. After confirming the correction angle M of the surgical osteotomy 900 of the tibia, the height of the osteotomy 900 can be fixed by a spreader 860. Then, the surgeon places a bone plate 700 to maintain the osteotomy 900 to complete the operation. The present invention can avoid ligament injury during surgery. It can also cut out an osteotomy 900 to resist the rotation of the bones 760 due to the movement. The present invention is designed according to a preoperative correction plan so that the surgical procedure can be simplified.

Wherein the first body component 100 further comprises a first correcting through-hole 160. The first correcting through-hole 160 is connected to the first body component 100 by a first bar 180. The second body component 200 further comprises a second correcting through-hole 260. The second correcting through-hole 260 is connected to the second body component 200 by a second bar 280. In the present invention, the first correcting through-hole 160 and the second correcting through-hole 260 are designed to confirm the angle at which the tibial osteotomy 900 is opened in high tibial osteotomy. For this reason, there is a correction angle L between the longitudinal axis 162 of the first correcting through-hole 160 and the longitudinal axis 262 of the second correcting through-hole 260. In high tibial osteotomy, an osteotomy 900 of the osteotomy has a preoperative planning correction angle M. When the tibia is opened by the first body component 100 and the second body component 200 with the correction angle M, the longitudinal axis 162 of the first correcting through-hole 160 and the longitudinal axis 262 of the second correcting through-hole 260 can coincide. An alignment bar 600 is passed through the first correcting through-hole 160 and the second correcting through-hole 260 to ensure the correction angle M. Firstly, the size of the aforementioned correction angle M is based on the correction angle M that the tibia needs to open in high tibial osteotomy. Secondly, the angle between the axis of the first correcting through-hole 160 and the axis of the second correcting through-hole 260 is determined according to the desired correction angle M and it is made. The alignment bar 600 can be inserted between the first correcting through-hole 160 and the second correcting through-hole 260 only when the tibia is opened at a preoperative planned correction angle M by the first body component 100 and the second body component 200.

Compared with the conventional technique, the osteotomy device with an extracorporeal alignment component is manufactured by three-dimensional printing according to the patient's bony CT data and the evaluation of the ideal cutting position and angle. The present invention is based on the different skeletal angles of each patient to create the overall structure of the osteotomy device with an extracorporeal alignment component. It constructs an integrally formed or combined solid instrument. The outer surface of the device can fit to the patient's bony anatomy 760 fully. The surgeon can perform the first bone cutting via the guide slot 500. The guide slot 500 helps the surgeon perform the operation accurately. It is also a reference for evaluating the direction and depth of bone cutting. The lateral guide fin 140 provides the other reference of the second bone cutting. The extracorporeal alignment component 300 and the extended barrier plate 240 further improve the osteotomy device in the prior art. Therefore, the present invention works for non-invasive assessment of the cutting direction during surgery, it can predict whether the placement (orientation/position) of the osteotomy device is correct and fix it in position and it can avoid over-cutting. In addition to improving the surgery itself, the present invention also standardizes the implementation of the surgeon's operation.

Various terms used in this disclosure should be construed broadly. For example, if an element "A" is to be coupled to or with element "B," element A may be directly coupled to element B or be indirectly coupled through, for example, element C. When the specification states that a component, feature, structure, process, or characteristic A "causes" a component, feature, structure, process, or characteristic B, it means that "A" is at least a partial cause of "B" but that there may also be at least one other component, feature, structure, process, or characteristic that assists in causing "B." If the specification indicates that a component, feature, structure, process, or characteristic "may", "might", or "could" be included, that particular component, feature, structure, process, or characteristic is not required to be included. If the specification refers to "a" or "an" element, this does not mean there is only one of the described elements.

The foregoing descriptions are preferred embodiments of the present invention. As is understood by a person skilled in the art, the aforementioned preferred embodiments of the present invention are illustrative of the present invention rather than limiting the present invention. The present invention is intended to cover various modifications and similar arrangements included within the spirit and scope of the appended claims, the scope of which should be accorded the broadest interpretation so as to encompass all such modifications and similar structures.

Many of the methods are described in their most basic form, but processes can be added to or deleted from any of the methods and information can be added or subtracted from any of the described messages without departing from the basic scope of the present invention. It will be apparent to those skilled in the art that many further modifications and adaptations can be made. The particular embodiments are not provided to limit the invention but to illustrate it. The scope of the embodiments of the present invention is not to be determined by the specific examples provided above but only by the claims below.

We claim:

1. A surgical method of using an osteotomy device with an extracorporeal alignment component comprising the steps of:
   placing the osteotomy device on a surface of a bone, wherein the osteotomy device includes a first body component, a second body component and a connecting member, said first body component is connected to said second body component via said connecting member,
   providing the extracorporeal alignment component including an engaging member and at least one aiming hole;
   engaging said engaging member of said extracorporeal alignment component with said connecting member of said osteotomy device;
   cutting along a guide slot formed between said first body component and said second body component to produce an osteotomy;
   spreading said osteotomy, wherein the step of spreading said osteotomy comprises inserting an alignment bar through both a first correcting through-hole and a second correcting through-hole, wherein a correction angle is formed between a longitudinal axis of said first correcting through-hole and a longitudinal axis of said second correcting through-hole; and
   placing a bone plate to maintain said spread osteotomy.

2. The surgical method of using an osteotomy device with an extracorporeal alignment component of claim 1, wherein said first body component has an upper guide fin.

3. The surgical method of using an osteotomy device with an extracorporeal alignment component of claim 2, wherein said second body component has a lower guide fin disposed below said upper guide fin.

4. The surgical method of using an osteotomy device with an extracorporeal alignment component of claim 3, wherein said guide slot is formed between said upper guide fin and said lower guide fin.

5. The surgical method of using an osteotomy device with an extracorporeal alignment component of claim 4, wherein said connecting member is disposed in said guide slot.

6. The surgical method of using an osteotomy device with an extracorporeal alignment component of claim 1, wherein after the step of engaging said engaging member with said connecting member, further comprising inserting at least one aiming bone pin in said at least one aiming hole to confirm the cutting direction.

7. The surgical method of using an osteotomy device with an extracorporeal alignment component of claim 1, further comprising:
   inserting an angle fixation bone pin in an angle fixation hole of said extracorporeal alignment component adjacent to said engaging member to fix an orientation of said osteotomy device with said extracorporeal alignment component.

8. The surgical method of using an osteotomy device with an extracorporeal alignment component of claim 7, wherein the step of inserting said angle fixation bone pin in said angle fixation hole comprises:
   inserting at least one fixation bone pins in a plurality of fixation holes of said first body component and said second body component to fix said osteotomy device with said extracorporeal alignment component.

9. The surgical method of using an osteotomy device with an extracorporeal alignment component of claim 8, wherein said first body component further comprises a lateral guide fin and the step of cutting along said guide slot comprises:
   cutting along said lateral guide fin.

10. The surgical method of using an osteotomy device with an extracorporeal alignment component of claim 9, wherein said lateral guide fin is disposed at an end of said upper guide fin.

11. The surgical method of using an osteotomy device with an extracorporeal alignment component of claim 10, wherein an extended barrier plate is disposed at an end of said lower guide fin to prevent over-cutting on said lateral guide fin.

12. The surgical method of using an osteotomy device with an extracorporeal alignment component of claim 11, wherein the step of cutting along said lateral guide fin or along said guide slot between said upper guide fin and said lower guide fin comprises:

inserting at least one osteotome.

13. The surgical method of using an osteotomy device with an extracorporeal alignment component of claim 12, wherein said first correcting through-hole is connected to said first body component by a first bar.

14. The surgical method of using an osteotomy device with an extracorporeal alignment component of claim 13, wherein said second correcting through-hole is connected to said second body component by a second bar.

15. The surgical method of using an osteotomy device with an extracorporeal alignment component of claim 1, wherein the step of inserting said alignment bar comprises:

maintaining a height of said osteotomy by a spreader.

* * * * *